United States Patent [19]
Edelson

[11] 4,428,744

[45] * Jan. 31, 1984

[54] METHOD AND SYSTEM FOR EXTERNALLY TREATING THE BLOOD

[75] Inventor: Richard L. Edelson, Roseland, N.J.

[73] Assignees: Frederic A. Bourke, Jr.; Eleanor F. Bourke; Richard L. Edelson; The Edelson Trust, all of East Norwalk, Conn.

[*] Notice: The portion of the term of this patent subsequent to Aug. 30, 1999 has been disclaimed.

[21] Appl. No.: 274,319

[22] Filed: Jun. 16, 1981

Related U.S. Application Data

[63] Continuation-in-part of Ser. No. 102,553, Dec. 11, 1979, Pat. No. 4,321,919, which is a continuation-in-part of Ser. No. 272,981, Jun. 12, 1981, Pat. No. 4,398,906.

[51] Int. Cl.$^3$ .............................................. A61M 1/03
[52] U.S. Cl. ....................................... 604/6; 128/1 R; 128/395; 128/DIG. 3; 422/44; 604/20; 604/28
[58] Field of Search ............ 128/214 B, 275.1, 207.22, 128/214 R, 214.2, 1.1, 1 R, 395, DIG. 3; 604/6, 604/20, 28

[56] References Cited

U.S. PATENT DOCUMENTS 3,325,641 6/1967 Jones .................................... 250/44

FOREIGN PATENT DOCUMENTS 2426473 12/1979 France .

OTHER PUBLICATIONS

Lieschlea et al., "Effects of 8–Methorypsoralen and UVA on Human Lymphocytes," *Demm Ris.*, 1977, pp. 293–298.

Parrish et al., Photochemotherapy of Psoraisis with Oral Methoxsalen and Longwave UV Light, *New England J. of Med.*, vol. 291, No. 23, Dec. 74, pp. 1207–1211.

*Primary Examiner*—George F. Lesmes
*Assistant Examiner*—Nancy A. B. Swisher

[57] ABSTRACT

A method and system are disclosed for externally treating human blood, with the objective of reducing the functioning lymphocyte population in the blood system of a human subject. According to the method, blood is withdrawn from the subject and passed through an ultraviolet radiation field in the presence of from about 1 nanogram to 100 micrograms per ml of blood, of a dissolved photoactive agent capable of forming photoadducts with lymphocytic-DNA, mobile cortisone receptors or antigen sites to thereby effect covalent bonding between the photoactive agent and the same, thereby inhibiting the metabolic processes of the lymphocytes or complexing them; and thereupon returning the irradiated blood to the subject. The withdrawn blood may be formed into an extracorporeal stream and flowed through a treatment station whereat the irradiation is effected, as for example by exposure to UV radiation; and such flow process may be conducted on a continuous basis. If desired, at least portions of the treated blood may then be separated, as for example by a continuous centrifuge, before returning the remaining diverted blood to the subject.

12 Claims, 5 Drawing Figures

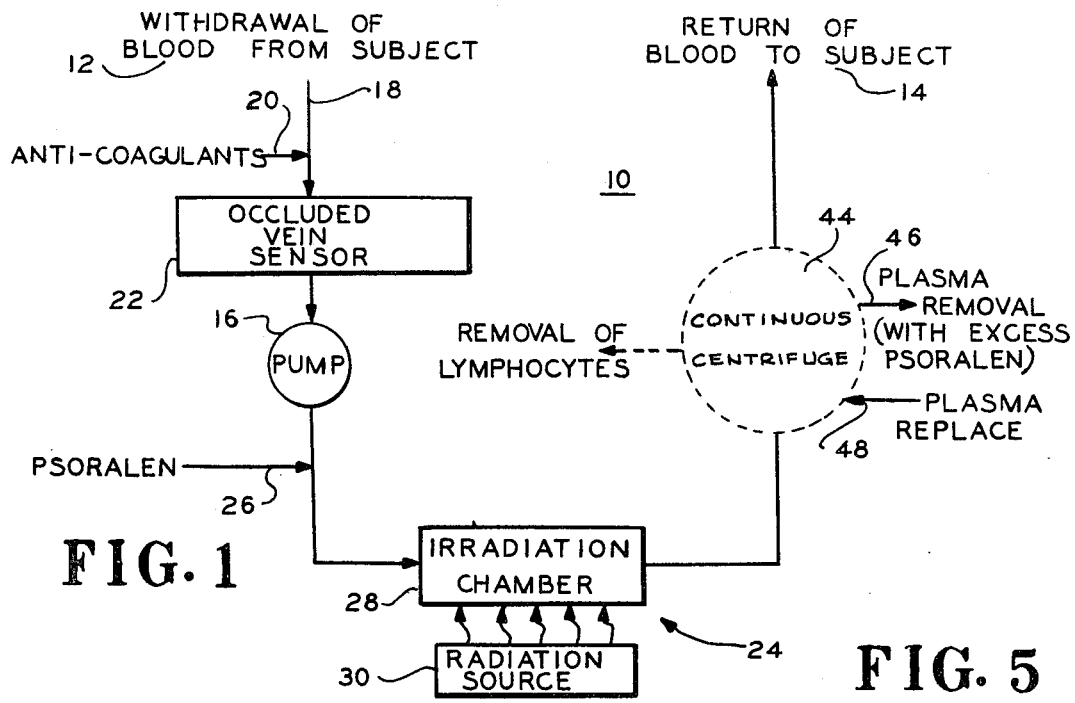
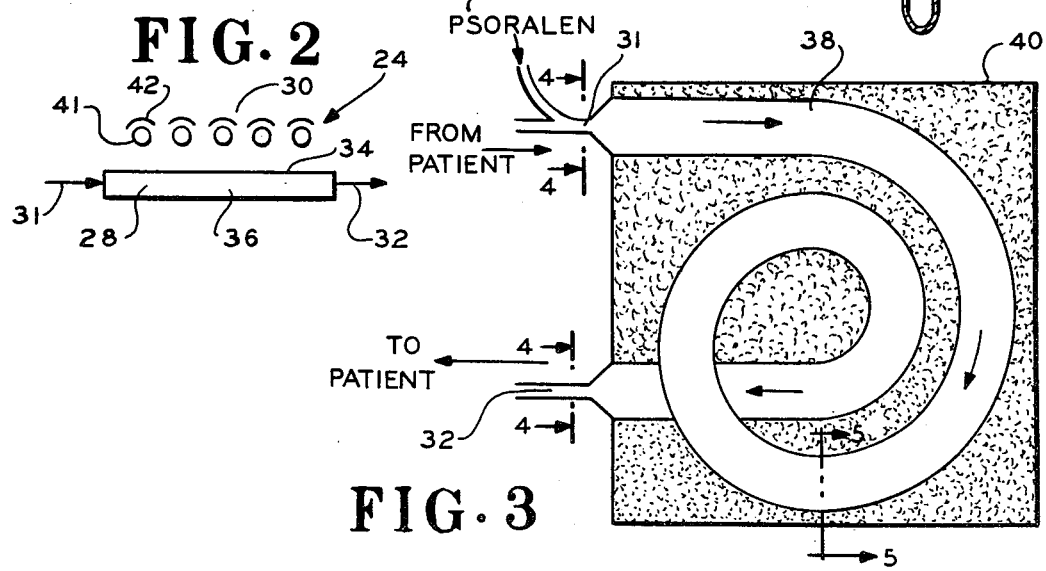

METHOD AND SYSTEM FOR EXTERNALLY TREATING THE BLOOD

This application is a continuation-in-part of my prior application Ser. No. 102,553, filed Dec. 11, 1979, now U.S. Pat. No. 4,321,919 and of my continuation-in-part to that application, Ser. No. 272,981, now U.S. Pat. No. 4,398,906, entitled METHOD FOR EXTERNALLY TREATING THE BLOOD, filed June 12, 1981.

This invention relates generally to a method and system for medical treatment of a living mammal, and more specifically relates to a method for treating the blood supply of a living subject with photoactive chemical agents which when activated form photoadducts with blood constituents for the purpose of reducing the functioning population of those constituents in the blood supply of the subject.

The method of this invention has particular applicability in a number of highly significant diseases, including certain forms of leukemia, where the population of certain types of leucocytes, including especially lymphocytes, increases inordinately in comparison to the other populations of nucleated cells in normal blood. While the excessive population of such lymphocytes represents a result of, rather than the underlying cause of the disese, the excessive lymphocyte population brings direct adverse effects to the patient if steps are not taken to reduce same. Complications thus rapidly develop which impair the functioning of bodily organs, and eventually a life-threatening situation is presented.

It should also be appreciated that excessive increase in the lymphocyte population of the blood supply can occur in other human maladies, in addition to lymphocytic leukemias. Thus, for example, such results can obtain in consequence of severe allergic reactions to administered agents, including drugs or the like, or in many other lymphocyte-mediated diseases.

In addition to the development over the years of pharmaceutical agents and the like, which may non-specifically reduce the lymphocyte population, e.g., by altering the underlying production rate of same, various techniques have from time to time been used in an effort to directly attack the problem, as for example by mechanically removing such lymphocytes from the blood supply. It is thus known, for example, to pass the blood supply through a continuous centrifuge, whereat one seeks to selectively remove lymphocytes to reduce the population of the latter in the thereby processed blood supply. In general, however, this method tends to be very inefficient, in part because the density differences between the blood fractions including the undesired lymphocytes and fractions which include desired blood components, is insufficient to assure that high percentages of the former are removed while retaining high proportions of the latter.

It is also well-known to treat diseases such as leukemia with high energy electromagnetic radiation, including in the X-ray region. While such treatment is often directed at internal bodily organis in which the blood cells are being generated, it has also been known to irradiate the blood supply with X-radiation at a point external to the body (the blood having first been withdrawn), whereby the radiation is not rendered directly incident on the body or internal organs of same. This method, while powerful, is indiscrimate, in that the intensely disruptive energy, in addition to destroying undesirable cells, disables or destroys components of the blood which are desired to be retained in vital status.

Among the pharmaceutical agents used to treat the excessive lymphocyte population resulting from leukemia are agents which are active against the lymphocyte itself. Cortisone is one such agent, its effectiveness, however, is limited as it does not completely suppress the aberrant metabolic activity of the malignant lymphocyte. The mechanism by which cortisone acts on lymphocyte cells is not fully understood, it is believed, however, to initially bind specifically to the cortisone receptors in the lymphocyte and to be carried by these mobile receptors to the cell's nucleus wherein it acts to alter the metabolic activity of the cell.

Certain other chemical agents are known or are believed to weakly bind to the nucleic acids of certain nucleated cells where they intercalate by forming molecular complexes involving low energy chemical interactions or intermolecular attractions, which generally are transient and insufficient to significantly affect the rate of DNA synthesis in the cell. The "psoralens" which are described in my earlier filed application, Ser. No. 102,553, of which this application is a continuation-in-part, are such chemicals.

Certain ligating proteins, known as antibodies, are also active against lymphocytes. The interaction of an antibody with a particular lymphocyte requires that the lymphocyte have a site or antigen which is geometrically and chemically receptive to a corresponding active site on the antibody. The forces which bind an antibody to an antigen consist of attractive forces including hydrogen bonding, apolar bonding, ionic interactions and Van der Waals interactions, the strength of which are inversely proportional to the distance between the interacting groups. Accordingly any structural variations in the lymphocyte membrane which serve to alter the geometry of the antigen can serve to prevent the binding of an antibody to the antigen. Further, once an antibody binds to an antigen on a cell, the cell may undergo "antigenic modulation" or altered cellular differentiation and thereby break the antibodies' bond on it and destroy the antibodies' affinity towards it. Where a lymphocyte's membrane has a structure which blocks the antibody from its antigenic site, the antibody while still attracted to the antigen will be unable to form any linkage of a permanent nature. Inasmuch as variations in cell structure are more the rule than exception with malignant cells, and "antigenic modulation" occurs in a high percentage of the antibody-cell antigen couplings, it has not been possible to effectively combat leukemia cells with antibodies.

The use of antibodies to permanently inactivate or remove immunogenic chemicals which may be found in the blood, such as undesirable natural antibodies, has also been hindered by the inability of an antibody to irreversibly or strongly complex with antigens.

The above-described pharmacologic interactions can be strengthened by use of photoactive chemicl analogues. Photoactive chemical agents are compounds containing one or more groups which are excited by incident ultraviolet radiation and which when activated have a tendency to form covalent linkages with nearby chemical groups. The reactivity of various photoactive agents varies from the chemically specific, which is the case with agents such as the psoralens, to agents having great reactivity toward virtually any group, which is the case with diazo and azide groups. The diazo and azide groups are the preferred photoactive moieties for imbuing chemical agents to be used in the invention with photoactivity which is essential in the method of the invention.

Until the present invention, photoactive chemical agents have been utilized only in very limited fashions. On a clinical level, one class of photoactive compounds, the psoralens, have been used to treat patients suffering from psoriasis. Other uses of these agents have been almost exclusively experimental investigations of cell physiology and chemistry, typical reports of which appear in the following articles in the *Annals of N.Y. Acad, Sci.* 346, "Photoaffinity Probes in the Antibody Combining Region," Richards, F. F. and Lifter, J., pp. 78–89; and "Photolabile Antibiotics As Probes of Ribosomal Structure and Function," Copperman, B. S., pp. 302–323.

SUMMARY OF THE INVENTION

Now, in accordance with the present invention, a method has been found which enables safe and effective reduction of the functioning population of certain blood constituents. More particularly, the method of the present invention enables the reduction of the functioning population of certain nucleated cells and undesirable antigenic chemical substances, such as undesirable autoreactive antibodies, in the blood supply of a human subject.

According to the method of invention, blood requiring such treatment is withdrawn from the subject and irradiated with UV radiation in the wavelength range of from about 2000 to 4000 Angstroms, and preferably from about 3200 to 4000 Angstroms (UVA), in the presence of an effective amount of a dissolved photoactive chemical agent of the type capable of intermolecular or chemical association with:

(1) the nucleic acids of nucleated blood cells,
(2) the steroid receptor sites of nucleated blood cells,
(3) the antigenic sites on nucleated blood cells,
(4) or the antigenic sites on immunogenic chemicals.

Upon irradiation, the photoactive chemical agent is induced to form a permanent photo-adduct with its associated site in or on the nucleated blood cell or immunogenic chemical whereby the destruction of the adducted constituent is assured. The irradiated blood is then returned to the subject.

When a photoactive chemical agent having an affinity for the nucleic acid of nucleated cells, such as lymphocytes, is employed in the present invention, the aforementioned intermolecular attractive forces draw the agent into an intercalated relationship with the nucleic acids of the lymphocytes. Prior to activation, the agent has little or no effect on the cell chemistry, however, upon irradiation the agent forms certain covalent attachments with the nucleic acids of the cell and thereby inhibits the metabolic functions of the cell. In this fashion, the cell's processes having been disrupted, and in particular its ability to divide, the death of the cell results.

The family of chemical known in the art as the psoralens and more fully described in my copening application, Ser. No. 102,553, filed Dec. 11, 1979, the disclosure of which is incorporated herein by reference, have been found to have the activity described and are deemed well suited for application in the present invention. Photoactive chemical agents, havin an affinity for DNA, such as the psoralens, when used in the invention have a highly desirable benefit in that the impairment and destruction of lymphocytes tends to be selective in certain diseases such as leukemia to the cells most sought to be reduced, by virtue of the fact that it is such cells which are undergoing the most intense metabolic activities to begin with, whereby they are the cells most subject to disablement by the present process.

Cortisone is a chemical agent having an affinity for particular receptors within the nucleated lymphocyte cell. As has been previously indicated, cortisone's applications in reducing the functioning lymphocyte population in patients suffering from leukemia have been less than entirely satisfactory. According to the present invention, however, cortisone can be utilized to treat leukemia in a new and far more effective fashion.

Prior to application in the invention, cortisone must first be rendered photoactive. Those skilled in the art will appreciate that the photoactivation of cortisone can be achieved using established chemical techniques. The particulars of that chemistry are not deemed to be within the scope of this invention, which is limited to a method whereby certain chemical agents can be employed to achieve previously unattainable reductions in the functioning population of certain blood constituents. Those skilled in the art will also recognize that employing established chemical procedures, including where necessary that of binding site protection, cortisone can be infused with a photoactive moiety at several positions and that the substituted cortisones can be evaluated and the homologue retaining the largest percentage of cortisone's normal biological activity easily determined. The chemistry of the aforedescribed photoactivation and determination of most active homologue is thoroughly discussed in the following articles:

(1) Katzenellenbogen, J. A., H. N. Myers and H. J. Johnson, Jr., 1973, *J.Org. Chem.* 38: 3525-33.
(2) Katzenellenbogen, J. A., H. J. Johnson, Jr. and H. N. Myers, 1973, *Biochemistry* 12: 4085-92.
(3) Katzenellenbogen, J. A., H. J. Johnson, Jr., K. E. Carlson and H. N. Myers, 1974, *Biochemistry* 13: 2896-94.

As these articles disclose, the photoactivation of steroids has been achieved with great success through the substitution of the photoactive moieties known as diazo and azide groups. These groups individually have a high degree of intrinsic photoactivity and that activity is retained when they are incorporated into another chemical agent, thereby rendering it photoactive.

Employing then, known techniques of photoderivatization, the 16-diazocortisone, which is preferred in the invention for retaining a high degree of its original pharmacological activity, can be synthesized in good yield by first nitrosating cortisone to give 16-oximocortisone, which can be converted into the 16-diazocortisone by chloramine oxidation. Other substituted cortisones may be derived by the nitration of cortisone using nitric acid in glacial acetic. The products of this nitration step are a number of azide derivatives, which can easily be separated by column chromatography. The reaction parameters employed to make these products can be found in enabling detail in the aforementioned Katzenellenbogen article in the *J. Org. Chem.* 38: 3525-33.

Photo-derivatized cotisone, having the preferred structure disclosed above or one of the other possible less preferred homologues, upon addition to the blood, readily enters the lymphocytes or other nucleated cells and associates itself with the cortisone receptor sites in those cells. After a suitable interval, calculated to allow a high percentage of the substituted cortisone to reach these receptor sites, typically in the range of 1 minute to 2 hours, and preferably 5–15 minutes, the blood containing a dosage of dissolved photoactivated cortisone that approximates that conventionally used in cancer treatment, typically in the range of from about 1 nanogram to 100 micrograms per ml of blood, is irradiated with UV radiation. Irradiation of the blood activates the photoactive moiety on the cortisone molecules in situ at the cortisone receptor sites and causes the formation of photo-adducts between the substituted cortisone and the cortisone receptor, as a consequence of which the receptor's ability to transmit cortisone vital to the continued metabolic activity of the cell is destroyed. Accordingly, a very large fraction of the cortisone receptors in the lymphocytes having been inactivated, the cells quickly become unable to function, and most particularly to divide, and their destruction rapidly follows.

Antibodies specific to particular blood constituents can be generated but, as has been indicated, it has not been possible to employ them with good results in reducing the population of malignant cells in the blood because of the variations in structure which are common with malignant cells and cellular phenomena such as antigenic modulation which enables cells to rid themselves of complexed antibodies. Thus, for example, antibodies specific for a particular type of malignant T-lymphocyte may be unable to complex with a large fraction of cells of that type in the blood, regardless of the antibodies having an affinity toward those cells, and a significant number of lymphocytes having been complexed by the antibodies shed their bound antigens breaking the antibodies' hold on them. According to the present invention, however, photoactivated antibodies can be utilized to reduce the functioning lymphoctye population to a previously unobtainable degree. Moreover, employing the method of the present invention photoactivated antibodies specifically reactive to other blood constituents such as, undesirable antibodies, can also be employed to reduce the population of those constituents in the blood with similar great effectiveness.

The methods whereby an antibody specific for a particular cell or immunogenic chemical may be produced and purified are well known in the art and need not be recited here, suffice it to say that large quantities of very specific monoclonal antibodies can be made by Hybridoma or by other established techniques.

The chemical techniques whereby an antibody desired for use in the present invention may be rendered photoactive are also well known to those skilled in the art. It will also be obvious to those skilled in the art, that virtually all antibodies have a number of sites suitable for photoactive derivatization. Methods whereby moieties foreign to an antibody may be added thereto without injuring the antibodies' ability to complex with its specific antigens, for example, have been disclosed in the *Handbook of Experimental Immunology*, Weir, D. M., pub. J. B. Lippincott, 1978, pp. 15.1–15.30. In furtherance of the objective of this invention, it is important that the process of derivatization not destroy the combining region of the antibody which is specific for the target cell. In this regard, it should be noted that in view of the number of potential sites for derivatization on most antibodies and the many different techniques whereby they may be infused with a photoactive moiety, such as the preferred diazo and azide groups, it will rarely be necessary to take the precaution of specifically protecting the combining region. Where, however, it is found that the combining region on an antibody would otherwise be destroyed by the photoderivatization of that antibody, established techniques of combining site protection and subsequent removal of the protecting group can be employed.

When photoactivated antibodies specifically reactive to some blood constituent, which for example in a preferred embodiment of this invention might be the malignant T-lymphocytes of a patient, are added to that patient's blood in the method of the present invention, they will very quickly complex with T-lymphocytes for which there exists the required correspondence of antibody combining region and cell antigenic site. Numerous antibodies, however, by reason of deficiencies in their own combining regions or in their target cells' receptors, while attracted to the target lymphocytes will be unable to form a true antibody-antigen complex. Upon irradiation with UV radiation, of a wavelength capable of activating the particular photoactive moiety which has been infused into the antibodies, the photoactive moieties on the antibodies which have complexed will preferentially form photo-adducts with the complexed cells, thereby permanently binding them to their complexed antibody and eliminating antigenic modulation as a means whereby the complex can be broken. Other antibodies which had previously failed to complex with any of the target cells to which they were attracted because of insufficient correspondence in their respective binding regions, will upon photoactivation preferentially form photo-adducts with those cells, thereby creating a photo-adduct complex where none had existed before. In the described fashion, dosages of photoactivated antibody approximating those conventionally employed in the treatment of maladies, in the order of from about 1 manogram to 100 micrograms per ml of blood, can be applied thereto with therapeutic effectiveness.

The foredescribed photo-induced antibody-antigen complexing is amplified by the infusion of multiple photoactive groups in to the antibody structure, for the presence of several photoactive moieties on the antibody increases the likelihood that a single antibody will be able to complex with more than one target cell. When such antibodies are employed according to the method of the invention, they have an enhanced tendency to form networks or chains of complexed cells which can be removed from the blood with particular facility.

It is also within the scope of this invention that antibodies specific to particular undesirable natural antibodies or other immunogenic chemicals can be rendered photoactive and used according to the method of the invention to form complexes which strongly bind those chemicals, enabling their removal from the body with a far greater efficiency than previously possible.

According to the method of the invention regardless of the type of photoactive chemical agent employed therein, blood withdrawn from a subject for treatment can be handled in batch form, but preferably is formed into an extracorporeal stream and passed through a treatment station whereat the irradiation is effected. Such a treatment station may take the form of an extended flattened tubular passageway, the walls of which are substantially transparent to the incident ultraviolet light (UV) used to activate the photoactive chemical agent. Typical radiation does range from about 0.1 to 100 joules per $cm^2$ and preferably from about 5 to 60 joules per $cm^2$ of blood surface whether the process is carried out on a continuous or discontinuous bases, and typical flow rates through the irradiation station can be in the range of from about 10 to 75 m./min.

Following treatment, the entire batch, or irradiated flow of diverted blood, can be returned to the patient. However, depending on which photoactive chemical agent was employed in the treatment of the blood, it may be preferable to filter on centrifuge the treated blood prior to its return to the patient. The instances in which such treatment would be deemed appropriate are more fully elucidated in the detailed description of this invention.

BRIEF DESCRIPTION OF THE DRAWINGS

The invention is diagrammatically illustrated, by way of example, in the drawings appended hereto, in which:

FIG. 1 is a schematic flow diagram illustrating a preferred embodiment of a system operating in accordance with the present invention;

FIG. 2 is a schematic elevational view of the irradiation station portion of the FIG. 1 system;

FIG. 3 is a plan view, schematic in nature, of one embodiment of the irradiation station of FIG. 2; and FIGS. 4 and 5 are cross-sectional views, taken along the lines 4—4 and 5—5 of FIG. 3, and illustrate in configurations of the flow passageway and the output passage for the FIG. 3 device.

DESCRIPTION OF PREFERRED EMBODIMENT

In FIG. 1 herein a schematic diagram appears of a system 10 in accordance with the present invention. Except for the irradiation station, the bulk of the components of system 10 are per se conventional and known in the art; and hence it is not deemed appropriate or necessary to vastly detail same.

As indicated in the Figure, blood may initially be withdrawn from the human subject, as at 12. Typically the blood is withdrawn via a donor needle, which may e.g. be emplaced at the right antecubital vein. In the showing of FIG. 1, it is assumed that the processing of blood pursuant to the invention is conducted on a continuous basis, i.e. for purposes of the present discussion the flow may be regarded as continuous from withdrawal at 12, to final return of the blood to the subject at 14. Such return 14 is typically effected via a recipient needle positioned in the left antecubital vein. Where the flow is indeed continuous in this manner, a typical blood flow utilizable in practice of the invention is in range of from about 10 to 75 ml/min. with a more preferred range being from about 40 to 50 ml/min. The indicated flow rates are effected by means of a pump 16, which is positioned in the extracorporeal blood flow stream generally indicated at 18, and may comprise one of numerous types of pumps used for blood flow treatment purposes, including such pumps as those available from Haemonetics Corp. under Model Designation 30.

As is known in the pertinent medical art, anti-coagulants are preferably injected into the extracorporeal blood flow stream at 20, i.e. close to the point of blood withdrawal. Such anti-coagulants can comprise solutions of acid citrate dextrose and/or of heparin, or of other known compositions useful for this purpose.

An occluded vein sensor 22 is preferably provided in stream 18 for purposes, as known in the art. Such sensor basically comprises a reservoir or buffer volume, the object of which is to prevent or inhibit generation or continued existence of bubbles in the blood flow stream.

Pursuant to a preferred mode of practicing the present invention, the photoactive chemical agent is preferably added to the blood of the human subject external to such subject; and thus as shown in the system 10 of FIG. 1, may be provided to the flowing blood downstream of pump 16, and just upstream of where the blood enters the irradiation station 24.

As has been discussed under the "Summary of Invention," the preferred photoactive chemical agents for use in the process of the invention are the psoralens, photoactivated cortisone, photoactivated antibodies specifically reactive to malignant lymphocytes and photoactivated antibodies specifically reactive to a patient's undesirable antibodies. As was also indicated, other photoactive chemical agents, are also utilizable in the method of the invention. The basic technique used in introducing photoactive chemical agents, is to dissolve same in an isotonic solution, which thereafter is directly injected into the flowing blood streams, as at 26. The agents are injected at a rate in comparison to the blood flow rate as to achieve a concentration in the blood thereafter passed to irradiation station 24 in the desired range, described for each of the chemical agents of the invention.

In the foregoing connection it should be appreciated that the primary objective of the operations thus far described is one of achieving the desired dissolved concentration of the photoactive chemical agent prior to introduction of the blood to the irradiation station. In accordance with a further aspect of the invention, it will therefore be appreciated that the said photoactive agent need not necessarily be directly introduced by injection into the extracorporeal blood stream 18 flowing in FIG 1. Rather, it is also acceptable to achieve the desired concentration of photoactive agent by orally or otherwise administering the compound directly to the patient. Where, for example pursuant to the invention, psoralen is orally administered, it can be provided in oral dosages of from about 0.6 to 1.0 mg per kg of body weight. The desired concentration range in the blood used for practice of the invention, is then achieved in about two hours from oral administration. Alternate modes of administration for the other photoactive chemical agents within the scope of this invention and the doses appropriate therefor will be apparent to those skilled in the art.

However, it is preferred to introduce the photoactive chemical agents of the invention to the extracorporeal stream (or to an extracorporeal batch volume) in order to achieve more exact concentration levels; and further, to avoid or minimize possible side effects and the like, which can occur from administration of any drug directly to the body system.

At irradiation station 24, consisting of an irradiation chamber 28 and radiation source 30, the blood now carrying in solution the desired concentration of photoactive chemical agent, is subjected to ultraviolet radiation (UV) and preferably UV radiation having the bulk of its spectral components in the preferred range for the activation of the particular photoactive agent being employed in the treatment being conducted. The materials of construction of the irradiation station 24 are selected so as not to block radiation in the desired portion of the UV spectrum.

In FIG. 2, a schematic elevational view appears of an irradiation station 24 of a type suitable for use with the invention. Such station consists of a blood treatment or irradiation chamber 28, having an inlet 31 and an outlet 32, enabling blood flow through the chamber, and a spaced source 30 or UV radiation. The chamber 28 can take various forms, with the principle requirement for same being that the wall 34 of same opposed to source 30, be substantially transparent to the incident UV radiation. The said chamber (or at least wall 34) can therefore typically be comprised of various substantially UV-transparent plastics, as are commonly used in tubing constructed for administration of standard intravenous solutions, such as polyvinyl chloride and the like.

In one preferred embodiment of irradiation chamber 28, which is easily adapted for use in both the continuous and batch modes of this invention, the device comprises a simple envelope which is irradiated from above and below. Accordingly in this embodiment, the blood to be treated flows through irradiation chamber 28 in central void 36 which is substantially of thin rectangular cross-section. The surface area of the chamber 28 is adapted in conjunction with the light sources so as to provide the blood contained therein within the desired radiation dose level. In an alternate embodiment, blood treatment chamber 28 has a configuration as shown in FIGS. 3, 4 and 5. In this instance a tubular coil 38, which in cross-section (FIG. 5) is flattened to a very elongated elipse, is fixedly maintained in or upon a support plate 40. The blood flow inlet 30 to the coil is of circular cross section, and in terms of FIG. 1 is at a point downstream of pump 16. The feed-in for the photoactive chemical agent is schematically depicted at 26. The highly flattened cross-section of the coil enables good flow for the blood passing through the coil, but more importantly, enables good exposure of the flowing blood to the incident UV radiation. The outlet 32 is again returned to a circular cross-section.

Regardless of the design selected for the chamber 28, it is preferred that the chamber be as thin as practicable. Chambers having a thickness in the range of from about 0.05 to 10 mm are within the range contemplated in the invention, with chamber thicknesses in the range of from about 0.05 mm to 1 mm preferred.

UV source 30 may comprise one or a plurality of side-by-side or otherwise arranged UV light sources 41, each of which may be backed by a reflector 42. The UV sources can comprise commercially available lamps, numerous types of which are known in the art.

By way of example, source 30 can comprise a single 1000 watt Hg lamp of the type available from Oriel Corporation of Stamford, Conn., under Model designation 6287. When used with appropriate filters this source provides a good relatively continuous spectrum of high intensity radiation between 3200 and 4000 Angstroms, with a peak emission at about 3650 Angstroms, which is preferred when psoralen is the photoactive agent being employed in the method of the invention. The said lamp with a suitable reflector can be positioned approximately 5 to 30 cm from chamber 28. With the flow rates utilized in accordance with one aspect of the invention, such a source will provide absorbed energy in the flowing blood within the range of interest for practicing the method of the invention.

The blood flow from irradiation station 24 proceeding as shown in FIG. 1 via outlet 32, can be directly returned to the subject at 14. Optionally, however, prior to returning the treated blood to the patient, it may be heat exchanged so as to adjust its temperature to that of the patient's circulating blood. Heat exchange as described is necessary whenever the treated blood, by consequence of its treatment, has attained a temperature substantially at variance with that of the patient.

Where the method of the invention has been employed to reduce the functioning lymphocyte population of the blood, employing either a DNA active agent, such as a psoralen, or a photoactivated cortisone, the treated lymphocytes upon return to the patient as a consequence of their treatment will be rapidly broken down and destroyed by the normal processes occuring in the patient. More specifically, by their treatment according to the aforementioned embodiments of the invention, the metabolic functions of the treated lymphocytes are impaired to the extent that with appropriate doses of photoactive agent and UV radiation a substantial percentage of the treated cells will be destroyed on a gradual basis over a period of days. A benefit of this feature of the invention is that it is thus possible to treat substantially the entire blood supply of a patient in a single treatment without causing the catastrophic overloading of the body's blood purification system which would otherwise result if the entire population of treated lymphocytes were to succumb to the treatment at the same time.

Where photoactivated antibodies specific to a malignant lymphocyte are employed in the other preferred embodiments of the invention, the blood returned to the subject will have its lymphocytes (or alternatively an undesirable antibody) complexed by the activated antibody and thus tagged for removal from the blood stream. Since, however, the photoactivated antibody complexes formed according to this embodiment of the invention are essentially completely formed prior to the exiting of the blood from the irradiation station 24, the blood must either be dosed, with relatively small amounts of activated antibody, so as not to shock or overload the patient's biological blood filtration system, or the treated blood must be filtered or centrifuged prior to its return to the patient.

Regardless of which photoactivated agent is employed in the invention or at what rate it is administered the burden placed upon the body's organ system can be further alleviated, by utilizing in conjunction with the present system, a continuous centrifuge 44 (or other filtration system), which device serves several functions.

It is to be noted that continuous centrifuges of the type here utilized, have been long employed in blood flow processing systems commercially available from several manufacturers, including Haemonetics Corporation of Braintree, Mass., and the IBM Corporation, Medical Products Division, of Monsey, N.Y. In the prior art systems in which such devices have been utilized all elements of FIG. 1 have been present, with the singularly important exception of the irradiation station 24. The function of the continuous centrifuge in such prior art systems has been one of separating excess lymphocytes or other blood components of interest. Where so used, a detriment of such system was the inefficiency of same, i.e. the centrifuging process can at best remove about 40 to 50% of the lymphocytes, and unfortunately also removes components which are in fact desired to be retained.

In the system 10 of the present invention, two functions can be performed by the continuous centrifuge 44. One of these, is removal of lymphocytes or other complexed blood constituents, as previously discussed. Because the present invention in its psoralens and cortisone treatment embodiments relies primarily on impairment of function of the lymphocytes to ultimately reduce the functioning population of same, the centrifuge 44 need not be relied upon to the extent that same has been in the aforementioned prior art arrangements. From a mechanical viewpoint, this implies that one need not work as close to the specific gravity interface between the lymphocyte fraction of the blood and the desirable fractions of the blood which one seeks to retain. Thus one can avoid undue separation of those desired fractions of the whole blood.

In the embodiments of the invention employing photoactivated antibodies, the antibody complexes formed will be easily separated from the other desirable blood fractions, whether by filtration or in the depicted centrifuge type device 44.

The continuous centrifuge 44, may further be utilized for an additional important purpose. In particular, some or virtually all of the blood plasma may be removed at 46 and replaced with fresh plasma at 48. This washing technique enables one to effectively withdraw the excess photoactive chemical agent compounds which may be present in the blood plasma, replacing the plasma at 46 with isotonic fluid free of the same. Thus, when the blood is returned to the subject at 14, it is substantially free of any excess chemical agent, i.e. other than those which combined with the treated blood constituent in the manner desired.

It should also be reemphasized that while the preferred mode of practicing the present invention, as illustrated in FIG. 1, contemplates a continuous operation, the blood treatment pursuant to the invention can be effected by batched techniques. Thus for example a distinct, fixed quantity of blood may initially be withdrawn from the subject. Such quantity or batch, may already have present therein the desired quantities of dissolved photoactive chemical agent, i.e. by prior administration to the patient; or the said agent may be admixed externally with the withdrawn blood. The said blood batch bearing the desired agent may then be provided to an irradiation station, where the desired quantity of UV energy is rendered incident upon same. During this process the batch of blood can be flowed through the station as previously discussed, or if the quantity of blood is appropriate and the blood treatment chamber 28 of appropriate dimensions, the batch can simply be treated under static conditions until the desired energy has been dissipated. Thereafter, the treated blood is taken from the irradiation station, and either centrifuged as above discussed, or directly returned to the subject.

The following additional chemical agents are known to interact with intact cells following exposure to UV and visible light. These agents may also be used in the system of this invention.

1. Ethidium and acridines (Yielding K.L. and Yielding L.W.: Photoaffinity labeling of DNA. *Annals of N.Y. Acad. Sci.* 346:368–378, 1980). —Also adriamycin, daunomycin, rubidazone.

2. Sulfonamides, sulfonylureas, phenothiazones, tetracyclines, coal tar derivatives, anthracene, pyridine, phenanthrene (Kornhauser A: Molecular aspects of phototoxicity. *Annals of N.Y. Acad. Sci.* 346:398–414, 1980).

3. Specifically reactive antibodies (Richard F. F. and Lifter J.: Photoaffinity probes in the antibody combining region. *Annals of N.Y. Acad. Sci.* 346:78–89, 1980).

The following example is included to illustrate the application of the method and system of this invention in bringing about a therapeutic reduction in the functioning population of a blood constituent in a human subject's blood supply.

Five hundred cubic centimeters of blood (500 cc) were drawn from a patient suffering from acute leukemia. This blood was held in a blood bag, and lines were run from the blood bag to the blood treatment system and then from that system back to the blood bag.

In this experiment, the system employed consisted of a pump and a multi-pass UVA Exposure Station, having an exposure chamber with a thickness of 1.0 mm and a total surface area of 0.312 square meters. The exposure chamber was irradiated from above and below by ultraviolet A light sources providing radiation having the bulk of its spectral components in the 3200 to 400 Angstrom range, with peak intensities at about 3600 to 3700 Angstroms. The level of radiation incident to the surfaces of the exposure chamber was measured at about 28.8 $J/cm^2/hr$.

A psoralen level in the blood to be treated of 100 nanograms/ml was achieved by oral administration of psoralen to the patient two (2) hours prior to the taking of the blood for this test. Subsequent to taking, the blood sample was dosed with 20 units of heparin sulfate per ml of blood, in order to prevent coagulation of the blood sample in the apparatus.

The white cell count of the blood sample, prior to commencement of the test, was 500,000/$mm^3$ which level compares very unfavorably with a normal count of 5000 cells/$mm^3$. Examination of the cells revealed that virtually all the cells in the sample were malignant T-lymphocytes.

In operation, blood was drawn from the blood bag at a rate of 40 cc/min., passed through the irradiation chamber and then returned to the blood bag. A sample was taken from the return line prior to the commencement of UVA irradiation and at one hour intervals thereafter, the last sample being taken 3 hours after commencement of irradiation. The samples were maintained in cultures from which aliquots were drawn for evaluation on the third, fourth, fifth and sixth days after irradiation.

Each aliquot drawn from the three irradiated blood samples was tested for total nucleated blood cells and the number of those cells remaining viable. The number of viable nucleated cells remaining in a sample was determined by treating it with trypan blue which is absorbed by dead nucleated cells and rejected by viable cells.

The data presented in the Table is organized as follows:

Column I—interval after irradiation until evaluation of cell count of the sample (in days).
Column II—nucleated cell count of sample at time of evaluation ($\times 10^4$).
Column III—total nucleated cell count (viable+-dead)/nucleated cell count at time zero (percent).
Column IV—viable nucleated cell count/total nucleated cell count at time zero (percent).

| TREATMENT OF 500 cc BLOOD SYSTEM | | | |
|---|---|---|---|
| I | II | III | IV |
| Control (Not-Irradiated) 6 | 94 | 94 | 86 |
| Sample 0 | 71 | 100 | 95 |
| Taken After 3 | 33 | 46 | 35 |
| 1 Hour of 4 | 35 | 49 | 28 |
| UVA 5 | 21 | 29 | 14 |
| Exposure 6 | 27 | 37 | 13 |

-continued
TREATMENT OF 500 cc BLOOD SYSTEM

| | I | II | III | IV |
|---|---|---|---|---|
| Sample | 0 | 125 | 100 | 100 |
| Taken After | 3 | 83 | 66 | 48 |
| 2 Hours | 4 | 47 | 37 | 21 |
| of UVA | 5 | 41 | 32 | 13 |
| Exposure | 6 | 13 | 10 | 2 |
| Sample | 0 | 137 | 100 | 97 |
| Taken After | 3 | 70 | 51 | 29 |
| 3 Hours | 4 | 43 | 31 | 12 |
| of UVA | 5 | 12 | 16 | 2 |
| Exposure | 6 | 9 | 7 | 1 |

From the above Table, it is apparent that the invention has produced a rapid destruction of the excess lymphocytes population in the treated blood, without observable clinically adverse effects on other blood constituents. By way of analysis, within six days after treatment according to the subject method the population of viable lymphocyte cells in each blood sample was appreciably reduced. More particularly, within six days after exposure in the described apparatus for periods of 1, 2 and 3 hours, the percentages of viable lymphocytes remaining in the treated blood were respectively reduced to 13, 2 and 1 percent of their original values. By way of comparison, a control sample which was not exposed to UVA had 86 percent of its lymphocyte population viable after the same amount of time.

While the present invention has been particularly described in terms of specific embodiments thereof, it will be understood in view of the present disclosure, that numerous variations upon the invention are now enabled to those skilled in the art, which variations yet reside within the scope of the present invention. Accordingly, the invention is to be broadly construed, and limited only by the scope and spirit of the claims now appended hereto.

What is claimed is:

1. A method for reducing the functioning population of nucleated cells in the blood supply of a human subject, comprising the steps of:
withdrawing blood from said subject, and irradiating said withdrawn blood with UV radiation in the presence of an effective amount of a dissolved photoactive chemical agent having an affinity for the nucleic acid of the nucleated blood cells and capable when activated by said UV radiation of forming photo-adducts with DNA, to thereby effect chemical bonding between said photoactive chemical agent and the nucleic acid of the nucleated cells, thereby altering the said nucleic acid and inhibiting the metabolic processes of said nucleated cells; and returning the irradiated blood to said subject.

2. A method in accordance with claim 1 wherein the nucleated cells are lymphocytes and said photoactive chemical agent is a psoralen.

3. A method in accordance with claim 1, wherein said withdrawn blood is formed into an extracorporeal flowing stream, passed through a treatment station whereat said irradiation is effected and returned to said subject in a continuous operation.

4. A method in accordance with claim 1, including the further step of separating at least portions of said nucleated cell population before returning said blood to said subject.

5. A method in accordance with claim 1, including the further step of separating at least portions of said nucleated cell population before returning said blood to said subject, by passing said bloodstream through a continuous flow centrifuge.

6. A method in accordance with claim 5 wherein excess quantities of said photoactive chemical agent are removed from the extracorporeal stream by withdrawing blood plasma at said centrifuge and replacing same with fresh photoactive chemical agent-free plasma.

7. A method in accordance with claim 1 wherein said blood is irradiated with photoenergy in the UVA wavelength range and at a radiation dose level of from about 0.1 to 100 joules/cm$^2$.

8. A method in accordance with claim 1 wherein said photoactive chemical agent is dissolved in said blood by mixing from about 1 nanogram to 100 micrograms of the same per ml of blood subsequent to withdrawing the blood from said subject.

9. A method in accordance with claim 1 wherein said photoactive chemical agent is dissolved in said blood by administering said agent to said subject.

10. A method for reducing the population of lymphocytes with intense metabolic activity in the blood supply of a human subject, comprising the steps of:
withdrawing blood from said subject, forming said blood into an extracorporeal stream, flowing said stream through a treatment station, irradiating said withdrawn blood in said treatment station with UV radiation to the presence of about 1 nanogram to 100 micrograms of a dissolved psoralen capable when activated by said UV radiation to effect chemical bonding between said psoralen and said lymphocytes, thereby selectively inhibiting the metabolic processes of said lymphocytes; and returning the irradiated blood to said subject.

11. The method of claim 10 including passing the blood from said extracorporeal stream through a centrifuge and separating out portions of said blood before returning the irradiated blood to said subject.

12. The method of claim 11 wherein said process is carried out continuously.

* * * * *

UNITED STATES PATENT AND TRADEMARK OFFICE
CERTIFICATE OF CORRECTION

PATENT NO. : 4,428,744

DATED : January 31, 1984

INVENTOR(S) : Richard L. Edelson

It is certified that error appears in the above-identified patent and that said Letters Patent is hereby corrected as shown below:

In the heading, the notice section should read -- The portion of the term of this patent subsquent to March 30, 1999 has been disclaimed.--

Signed and Sealed this

Fifteenth Day of September, 1987

Attest:

DONALD J. QUIGG

*Attesting Officer*     *Commissioner of Patents and Trademarks*

UNITED STATES PATENT AND TRADEMARK OFFICE

CERTIFICATE EXTENDING PATENT TERM
UNDER 35 U.S.C. 156

Patent No.    : 4,428,744

Dated         : January 31, 1984

Inventor(s)   : Richard L. Edelson

Patent Owner  : Frederic A. Bourke, Jr.; Eleanor F. Bourke;
                Richard L. Edelson; The Edelson Trust This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of 652 days with all rights pertaining thereto as provided by 35 USC 156(b).

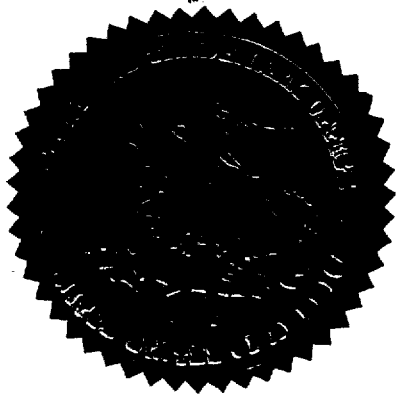

I have caused the seal of the Patent and Trademark Office to be affixed this Twenty-first day of April 1988.

Donald J. Quigg

Assistant Secretary and Commissioner of Patents and Trademarks